United States Patent
Lee et al.

(10) Patent No.: US 8,865,181 B1
(45) Date of Patent: Oct. 21, 2014

(54) **EXTRACTING METHOD OF *ANTRODIA CINNAMOMEA***

(71) Applicant: Kang Li Biotech Co., Ltd., Kaohsiung (TW)

(72) Inventors: Shih-Chiang Lee, Kaohsiung (TW); Shorong-Shii Liou, Kaohsiung (TW); I-Min Liu, Kaohsiung (TW); Ren-Jye Wang, Kaohsiung (TW); Hsiu-Tz Pan, Kaohsiung (TW)

(73) Assignee: Kang Li Biotech Co., Ltd., Kaoshiung (TW)

( * ) Notice: Subject to any disclaimer, the term of this patent is extended or adjusted under 35 U.S.C. 154(b) by 54 days.

(21) Appl. No.: 13/871,557

(22) Filed: Apr. 26, 2013

(51) Int. Cl.
| | | |
|---|---|---|
| *A61K 36/06* | (2006.01) | |
| *A61K 36/09* | (2006.01) | |
| *A61K 31/56* | (2006.01) | |
| *A61K 36/07* | (2006.01) | |

(52) U.S. Cl.
CPC ..................................... *A61K 36/07* (2013.01)
USPC ....................... 424/195.15; 514/169; 514/182

(58) Field of Classification Search
CPC ... A61K 36/06; A61K 36/07; A61K 2236/10; A61K 2236/33; A61K 2236/333
USPC .................................................... 424/195.15
See application file for complete search history.

(56) References Cited

U.S. PATENT DOCUMENTS

| | | | |
|---|---|---|---|
| 7,838,264 B2 | 11/2010 | Wang et al. | |
| 7,994,158 B2 | 8/2011 | Chen et al. | |
| 8,122,636 B2 | 2/2012 | Chen et al. | |
| 2009/0227001 A1* | 9/2009 | Wang et al. | 435/244 |
| 2009/0318400 A1 | 12/2009 | Chen et al. | |
| 2010/0210869 A1 | 8/2010 | Wu et al. | |
| 2012/0029069 A1* | 2/2012 | Lee et al. | 514/464 |
| 2012/0190871 A1* | 7/2012 | Wu et al. | 552/541 |

FOREIGN PATENT DOCUMENTS

| | | |
|---|---|---|
| JP | H 02-211202 A | 8/1990 |
| JP | H 05-124973 A | 5/1993 |
| JP | 2000-236889 A | 9/2000 |
| JP | 2007-153740 A | 6/2007 |

* cited by examiner

*Primary Examiner* — Chris R Tate
*Assistant Examiner* — Russell Fiebig
(74) *Attorney, Agent, or Firm* — Muncy, Geissler, Olds & Lowe, P.C.

(57) ABSTRACT

An extracting method of *Antrodia cinnamomea*, being apt to improve extraction rate of dehydrosulphurenic acid, comprises: soaking a sample of raw *Antrodia cinnamomea* in a salt solution, with the sample of raw *Antrodia cinnamomea* absorbing the salt solution, to obtain a soaked *Antrodia cinnamomea*; and further soaking the soaked *Antrodia cinnamomea* in an alcohol solvent, and obtaining an extract of *Antrodia cinnamomea* through sonication.

7 Claims, 4 Drawing Sheets

EXTRACTING METHOD OF *ANTRODIA CINNAMOMEA*

BACKGROUND OF THE INVENTION

1. Field of the Invention

The present invention relates to an extracting method of *Antrodia cinnamomea* and, more particularly, to an extracting method of *Antrodia cinnamomea* which is capable of improving extracting rates of dehydrosulphurenic acid from *Antrodia cinnamomea*.

2. Description of the Related Art

*Antrodia cinnamomea* is a genus of fungi in the family Fomitopsidaceae, and which is found on *Cinnamomum kanehirae* in temperate and boreal forests. *Antrodia cinnamomea* is a precious and endemic medical material in Taiwan, being rich in active substances, such as triterpenoids being effective on anti-cancer, hepatoprotection and lowering blood pressure and polysaccharide as inflammation modulator.

Among those active substances, dehydrosulphurenic acid (as shown in FIG. 1) is one of particular triterpenoids of *Antrodia cinnamomea*, and which is subjected to lanostanes, as an intermedium in a metabolic pathway from squalene to sterol. In this way, dehydrosulphurenic acid is easy to interfere with the biochemical paths of metabolism of cholesterol and generation of mambrance, and therefore which plays a critical role in cell cycle and physiological metabolism. Also, it is reported that dehydrosulphurenic acid can lead to apoptosis of cancer cells and mitotic catastrople, thereby being dramatically effectively in treating of pancreas cancer and acute myeloid leukemia.

For the sake of increasing a nutritive value of *Antrodia cinnamomea*, conventional extracting method of *Antrodia cinnamomea* makes triterpenoids therein being released from the *Antrodia cinnamomea* to a solvent, with an extract of *Antrodia cinnamomea* full of nutrition being obtained through condensation and drying. In this way, people in need only require a small of the extract of *Antrodia cinnamomea* to obtain therapeutic effects provided by a great amount of raw *Antrodia cinnamomea*.

Generally, conventional extracting methods of *Antrodia cinnamomea* are divided to extractions of water and extractions of organic solvent due to various selections of solvent.

Conventional extractions of water extract raw *Antrodia cinnamomea* with water being an extracting solvent, to obtain an extract of *Antrodia cinnamomea*. However, due to poor solubility of triterpenoids, the extract of *Antrodia cinnamomea* obtained by said conventional extractions of water usually has a poor amount of triterpenoids.

Conventional extractions of organic solvent extract raw *Antrodia cinnamomea* with organic solvents (used as extracting solvents), such as alcohols, esters, alkanes, and alkyl halides, to obtain an extract of *Antrodia cinnamomea* after removing the organic solvents through distillation at a low temperature. In comparison with said conventional extractions of water, it is able to obtain triterpenoids at a high amount, but it is still poor in releasing dehydrosulphurenic acid.

Thus, it is a need to improve the conventional extracting method of *Antrodia cinnamomea*.

SUMMARY OF THE INVENTION

An objective of the present invention is to provide an extracting method of *Antrodia cinnamomea*, which can obtain an extract of *Antrodia cinnamomea* having increased amount of dehydrosulphurenic acid therein, thereby, improving extraction rates of dehydrosulphurenic acid from *Antrodia cinnamomea*.

The present invention fulfills the above objective by providing an extracting method of *Antrodia cinnamomea* comprising: soaking a sample of raw *Antrodia cinnamomea* in a salt solution, with the sample of raw *Antrodia cinnamomea* absorbing the salt solution, to obtain a soaked *Antrodia cinnamomea*; and further soaking the soaked *Antrodia cinnamomea* in an alcohol solvent, and obtaining an extract of *Antrodia cinnamomea* through sonication.

Preferably, the soaked *Antrodia cinnamomea* is further steamed at 110 to 150° C., 1 to 3 $kg/cm^2$ before the further soaking, and impurities on the sample of raw *Antrodia cinnamomea* are removed before the soaking.

Preferably, the soaked *Antrodia cinnamomea* is steamed at 121° C., 1 $kg/cm^2$ for 15 to 60 minutes.

Preferably, the salt solution is 2% sodium chloride solution, with the sample of raw *Antrodia cinnamomea* in 500 g being soaked in 1 L, sodium chloride solution, and the alcohol solvent is 95% ethanol.

Preferably, the sample of raw *Antrodia cinnamomea* is selected from carpophore of *Antrodia cinnamomea*.

In the extracting method of *Antrodia cinnamomea* of the present invention, increased amount of dehydrosulphurenic acid is released in the alcohol solvent since the sample of raw *Antrodia cinnamomea* has been soaked in the salt solution, so as to obtain an extract of *Antrodia cinnamomea* having an increased amount of dehydrosulphurenic acid.

The present invention will become clearer in light of the following detailed description of illustrative embodiments of this invention described in connection with the drawings.

BRIEF DESCRIPTION OF THE DRAWINGS

The illustrative embodiments may best be described by reference to the accompanying drawings where.

Figure 1:
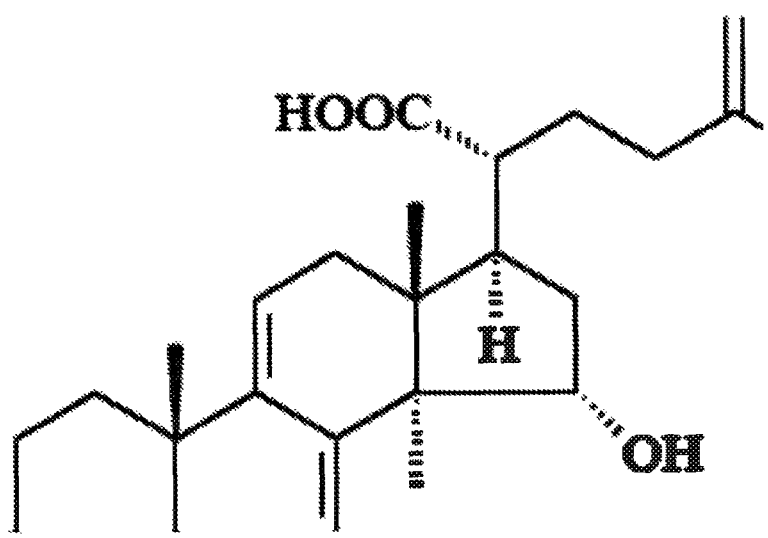
FIG. 1 shows chemical structure of dehydrosulphurenic acid.

All figures are drawn for ease of explanation of the basic teachings of the present invention only; the extensions of the figures with respect to number, position, relationship, and dimensions of the parts to form the preferred embodiments will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

DETAILED DESCRIPTION OF THE INVENTION

A preferable embodiment of the present patent invention refers to an extracting method of *Antrodia cinnamomea* comprising following steps: soaking a sample of raw *Antrodia cinnamomea* in a salt solution, with the sample of raw *Antrodia cinnamomea* absorbing the salt solution, to obtain a soaked *Antrodia cinnamomea*; and further soaking the soaked *Antrodia cinnamomea* in an alcohol solvent, and obtaining an extract of *Antrodia cinnamomea* through sonication.

Specifically, the sample of raw *Antrodia cinnamomea* in a quantified amount is soaked in a quantified amount of the salt solution, in order to obtain the soaked *Antrodia cinnamomea*. In the present embodiment, impurities on the sample of raw *Antrodia cinnamomea* can be previously removed, followed by soaking the raw *Antrodia cinnamomea* in the salt solution, in order to avoid interference of extraction caused by such impurities. The salt solution can be 2% sodium chloride solution due to easy obtaining and a low price thereof. With such, a cost of the extraction is decreased but therapeutic properties of *Antrodia cinnamomea* are increased through the soaking in the sodium chloride solution. In the present embodiment, the sample of raw *Antrodia cinnamomea* is soaked in the sodium chloride solution, preferably being soaked in an airtight container, so that external impurities will not contaminate the sodium chloride solution. In this way, the soaked *Antrodia cinnamomea* can be obtained via immersing the sample of raw *Antrodia cinnamomea* in the sodium chloride solution with the sodium chloride solution, with the sodium chloride solution infiltrating in the sample of raw *Antrodia cinnamomea*. As an example, in the present embodiment, the sample of raw *Antrodia cinnamomea* in 500 g are prepared, with impurities thereon being removed, and soaked in 1 liter of the sodium chloride solution for 24 hours to obtain the soaked *Antrodia cinnamomea*.

Next, the soaked *Antrodia cinnamomea* is further soaked in the alcohol solvent, and obtained the extract of *Antrodia cinnamomea* through sonication. In the present preferable embodiment, the alcohol solvent can be 95% ethanol, which is capable of releasing a high amount of triterpenoids from *Antrodia cinnamomea*. Also, the ethanol solvent can react with inorganic substances of *Antrodia cinnamomea* to generate highly soluble compounds in crystallized form, thereby increasing solubilities of those inorganic substances. Preferably, 5 g of the soaked *Antrodia cinnamomea* is collected and soaked in 600 ml ethanol, followed by extracting the soaked *Antrodia cinnamomea* at 25° C. via sonication at 40 KHz, with active substances (triterpenoids for example) in the soaked *Antrodia cinnamomea* being released from the soaked *Antrodia cinnamomea* and dissolved in the ethanol. Preferably, the soaked *Antrodia cinnamomea* is extracted for 8 hours, repeatedly extracted for three times, in particular, so that the extract of *Antrodia cinnamomea* is obtained with an increased total extraction rate. Moreover, the extract of *Antrodia cinnamomea* can be further lyophilized at −55° C. and 0 torr to obtain a condensed extract of *Antrodia cinnamomea*.

Preferably the soaked *Antrodia cinnamomea* can be steamed at a confined space of 110 to 150° C. and 1 to 3 kg/cm$^2$ before the soaking of ethanol and extracting, to dramatically increase the release of dehydrosulphurenic acid from *Antrodia cinnamomea*. Precisely, in the present embodiment, the soaked *Antrodia cinnamomea* can be steamed at an apparatus or equipment being adjustable in a temperature and a pressure thereof, (such as autoclaves), with the apparatus or equipment providing the confined space and controlling a temperature and a pressure of the confined space. In the present embodiment, the soaked *Antrodia cinnamomea* is steamed at 110° C. to 150° C. and 1 to 3 kg/cm$^2$ for 15 to 60 minutes in an autoclave having an adjustable temperature and pressure. Wherein, once the steaming is carried out at a temperature lower than 110° C., it is poor in extracting triterpenoids. On the other hand, if the steaming is carried out at a temperature higher than 150° C., active substances of the *Antrodia cinnamomea* are easy to damage at a high temperature. Therefore, in order to provide a temperature ranged from 110° C. to 150° C., it is necessary to control the pressure at 1 to 3 kg/cm$^2$ via the confined space, as the temperature being difficult to increase while the pressure is lower than 1 kg/cm$^2$ and the temperature being over high while the pressure exceeds 3 kg/cm$^2$. As an example, in the present embodiment the soaked *Antrodia cinnamomea* is steamed at 1210° C. and 1 kg/cm$^2$ for 15 to 60 minutes, till the soaked *Antrodia cinnamomea* coloring to dark red, so as to obtain a steamed *Antrodia cinnamomea*. Next, the steamed *Antrodia cinnamomea* is further soaked in the alcohol solvent to obtain the extract of *Antrodia cinnamomea*. Through steaming the soaked *Antrodia cinnamomea* in the confined space, vapor are not allow to escape from the confined space, not only being easy to control a temperature and a pressure therein, but also increasing the temperature of the vapor to more than 110° C. by increasing the boiling point of water under a high pressure provided by the confined space. Accordingly, the soaked *Antrodia cinnamomea* is steamed at a high temperature and a high pressure in the confined space, with the soaked *Antrodia cinnamomea* being full steamed and turning to dark red in a short period, thereby decreasing the steaming time, increasing the efficiency the steaming but saving the cost.

For proving said extracting method of *Antrodia cinnamomea* truly can increase dehydrosulphurenic acid in the extract of *Antrodia cinnamomea*, following tests of HPLC are carried out.

Specifically, in the present test, various extracts of *Antrodia cinnamomea* as shown in TABLE 1 are provided, including group A1, being an extract of *Antrodia cinnamomea* obtained by soaking a sample of raw *Antrodia cinnamomea* in the ethanol solvent; group A2, being an extract of *Antrodia cinnamomea* obtained by soaking a soaked *Antrodia cinnamomea* in the ethanol solvent; group A3, being an extract of *Antrodia cinnamomea* obtained by steaming a soaked *Antrodia cinnamomea* for 15 minutes, and then soaking in the ethanol solvent; group A4, being extract of *Antrodia cinnamomea* obtained by steaming a soaked *Antrodia cinnamomea* for 30 minutes, and then soaking in the ethanol solvent; group A5, being extract of *Antrodia cinnamomea* obtained by steaming a soaked *Antrodia cinnamomea* for 60 minutes, and then soaking in the ethanol solvent. Next, each extract of *Antrodia cinnamomea* in 0.2 g are collected respectively in a spiral tube, followed by adding 5 ml methanol in the spiral tube, sonicating for 15 minutes and centrifuging at 3000 rpm for 10 minutes. After that, suspension in each spiral tube are collected and transfer to a clean tube, with each clean tube being heated to dry at 100° C. water bath.

TABLE 1

Extracts of *Antrodia cinnamomea* in Each Groups

Figure 2A:
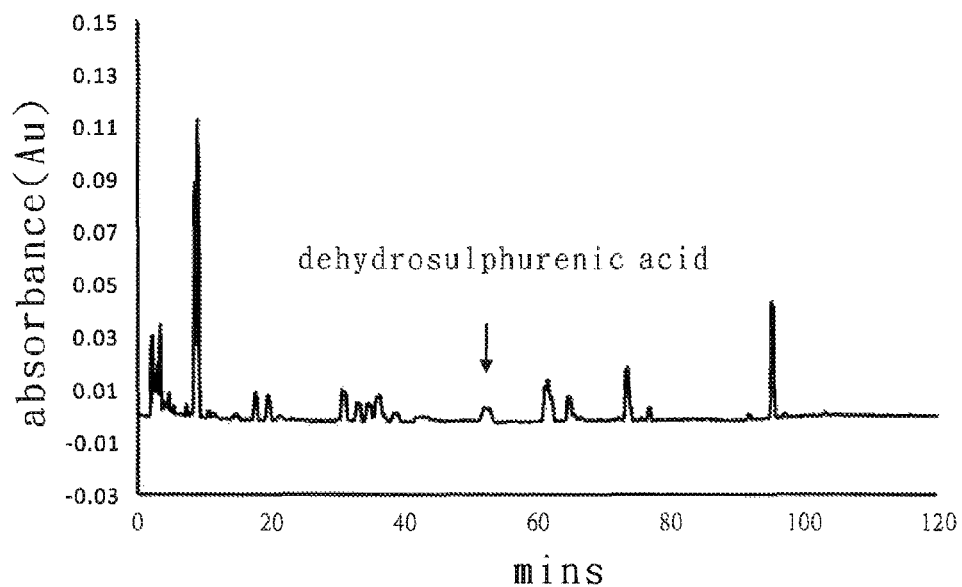
FIG. 2A shows HPLC data of an extract in group A1.
Figure 2B:
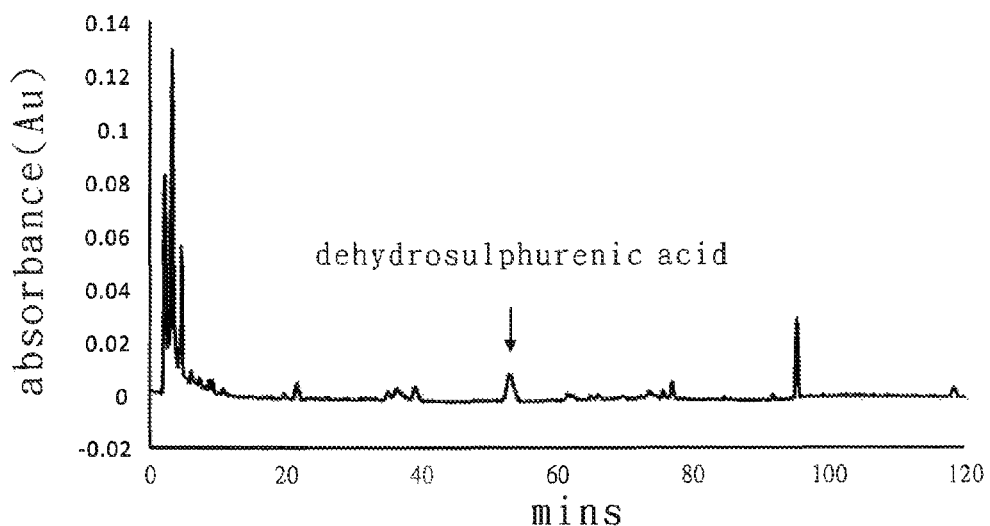
FIG. 2B shows HPLC data of an extract in group A2.
Figure 2C:
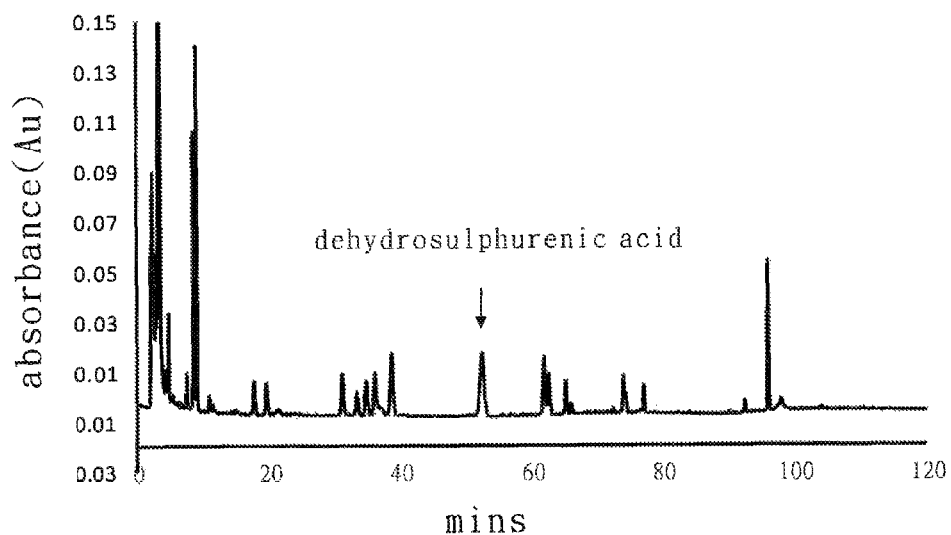
FIG. 2C shows HPLC data of an extract in group A3.
Figure 2D:
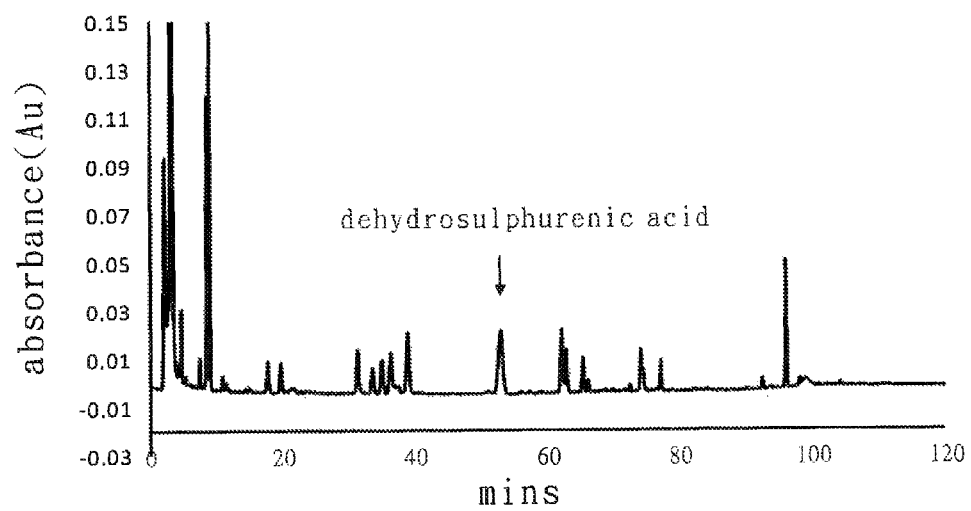
FIG. 2D shows HPLC data of an extract in group A4.
Figure 2E:
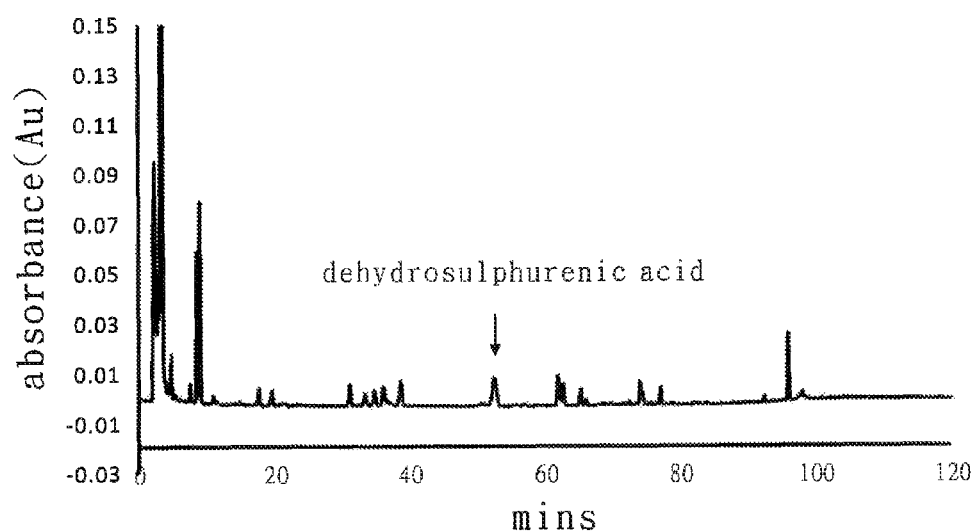
FIG. 2E shows HPLC data of an extract in group A5.

| Groups | Soaking Times (hr) | Steaming Times (min) | Soaking in Ethanol | Data |
|---|---|---|---|---|
| A1 | 0 | 0 | + | FIG. 2A & TABLE 3 |
| A2 | 24 | 0 | + | FIG. 2B & TABLE 3 |
| A3 | 24 | 15 | + | FIG. 2C & TABLE 3 |
| A4 | 24 | 30 | + | FIG. 2D & TABLE 3 |
| A5 | 24 | 60 | + | FIG. 2E & TABLE 3 |

As following, each tube is analyzed by purospher STAR RP-18e (5 μm) HPLC column (250 mm×4.6 mm; Merck) under 254 nm, with acetonitrile (ACN) and 0.085% phosphate buffer being a mobile phase in the test and with a flow velocity of the mobile phase being 1 ml/min.

TABLE 2

| | Conditions of HPLC | | |
|---|---|---|---|
| | Eluting Times | Mobile Phase | |
| Stages | (mins) | ACN (%) | Phosphate buffer (%) |
| a | 0 | 40 | 60 |
| b | 30 | 47 | 53 |
| c | 50 | 47 | 53 |
| d | 100 | 100 | 0 |
| e | 120 | 100 | 0 |

With reference to FIGS. 2A to 2E and TABLE 3, the extract of *Antrodia cinnamomea* obtained by soaking a sample of raw *Antrodia cinnamomea* in the sodium chloride solution and further soaking the sample of raw *Antrodia cinnamomea* in the ethanol solution (A2) has decreased amount of antcin K, antcin C, zhankuic acid C zhankuic acid A and dehydroeburicoic acid but has four times increase of dehydrosulphurenic acid, in comparison with that of the extract of A1. Moreover, the extracts of *Antrodia cinnamomea* obtained by soaking a sample of raw *Antrodia cinnamomea* in the sodium chloride solution, steaming at a high temperature for 15, 30, 60 minutes, and further soaking the sample of raw *Antrodia cinnamomea* in the ethanol solution respectively (A3, A4 and A5) has 6, 5.5 and 3 times increase of dehydrosulphurenic acid, in comparison the extract of A1 respectively.

TABLE 3

| | Contents of Dehydrosulphurenic Acid in Each Extract | | | | | |
|---|---|---|---|---|---|---|
| | Reacting Times | Ratios of Peak Area (%) | | | | |
| Substances | (min) | A1 | A2 | A3 | A4 | A5 |
| Antcin K | 8.880 | 13.697 | 1.074 | 6.118 | 6.067 | 4.336 |
| | 9.360 | 18.334 | 1.525 | 8.187 | 8.344 | 5.962 |
| Antcin C | 31.220 | 4.176 | 0.143 | 2.036 | 1.984 | 1.334 |
| | 33.373 | 2.428 | 0.218 | 1.212 | 1.170 | 0.787 |
| Zhankuic acid C | 35.113 | 2.100 | 1.200 | 1.836 | 1.623 | 1.048 |
| | 36.493 | 2.736 | 2.964 | 2.798 | 2.447 | 1.156 |
| Dehydrosulphurenic acid | 53.187 | 1.118 | 5.295 | 6.085 | 5.582 | 3.025 |
| Zhankuic acid A | 61.493 | 2.963 | 0.554 | 2.789 | 2.713 | 1.851 |
| | 62.160 | 5.709 | 0.538 | 1.854 | 1.804 | 1.240 |
| Dehydroeburicoic acid | 95.347 | 10.952 | 5.778 | 4.671 | 3.921 | 2.815 |

It is shown that, in the preferable embodiment of the extract method of *Antrodia cinnamomea*, the release of dehydrosulphurenic acid is dramatically increased through the soaking of the salt solution. Additionally, the steaming of the soaked *Antrodia cinnamomea*, steaming for 15 minutes in particular, can further enhance the release of dehydrosulphurenic acid.

In summary, through the present invention, the extracting method of *Antrodia cinnamomea* improves the release of dehydrosulphurenic acid from the *Antrodia cinnamomea* to the ethanol solvent through soaking the sample of raw *Antrodia cinnamomea* in the salt solution, so as to obtain the extract of *Antrodia cinnamomea* having an increased amount of dehydrosulphurenic acid.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A method of producing an extract of *Antrodia cinnamonmea* with a high content of dihydrosulphurenic acid comprising the steps of:
   (a) soaking a sample of raw *Androdia cinnamomea* in a sodium chloride solution for a sufficient amount of time to absorb the solution and obtain a salted *Antrodia cinnamomea* product,
   (b) steaming the salted product of step (a) for 15 to 60 minutes at 110-150° C. at 1-3 kg/cm$^2$,
   (c) soaking the steamed product of step (b) in an ethanol solution for a sufficient time to produce an extraction mixture,
   (d) sonicating the mixture produced in step (c) to produce the *Antrodia cinnamomea* extract with high levels of dihydrosulphenic acid.

2. The method of claim 1, wherein impurities on the sample of raw *Antrodia cinnamomea* are removed before the soaking.

3. The method of claim 1, wherein the soaked *Antrodia cinnamomea* is steamed at 121° C., 1 kg/cm$^2$.

4. The method of claim 1, wherein the sodium chloride solution is a 2% sodium chloride solution.

5. The method of claim 4, wherein the sample of raw *Antrodia cinnamomea* is 500 g and is soaked in 1 L sodium chloride solution.

6. The method of claim 1, wherein the ethanol solution is 95% ethanol.

7. The method of claim 1, wherein the sample of raw *Antrodia cinnamomea* is obtained from carpophore of *Antrodia cinnamomea*.

* * * * *